United States Patent [19]

Wife et al.

[11] Patent Number: 4,565,892

[45] Date of Patent: Jan. 21, 1986

[54] PROCESS FOR THE PREPARATION OF BISPHOSPHINE DIOXIDES

[75] Inventors: Richard L. Wife; Aart B. van Oort; Petrus W. N. M. van Leeuwen; Johannes A. van Doorn, all of Amsterdam, Netherlands

[73] Assignee: Shell Oil Company, Houston, Tex.

[21] Appl. No.: 562,620

[22] Filed: Dec. 19, 1983

[30] Foreign Application Priority Data

Dec. 20, 1982 [GB] United Kingdom ................. 8236147

[51] Int. Cl.$^4$ ............................................. C07F 9/53
[52] U.S. Cl. ...................................... 568/14; 260/971
[58] Field of Search ........................... 568/14; 260/971

[56] References Cited

U.S. PATENT DOCUMENTS

| | | | |
|---|---|---|---|
| 2,875,231 | 2/1959 | McConnell et al. | 260/970 |
| 2,957,931 | 10/1960 | Hamilton et al. | 260/970 X |
| 3,145,227 | 8/1964 | Grayson et al. | 568/14 X |
| 3,370,030 | 2/1968 | Cannelongo | 568/14 X |
| 3,458,581 | 7/1969 | Wu | 568/14 |
| 3,699,195 | 10/1972 | Randall et al. | 260/970 |
| 3,780,112 | 12/1973 | Weinberg et al. | 568/14 |
| 3,932,290 | 1/1976 | Koch et al. | 260/970 X |

OTHER PUBLICATIONS

Bridges et al., J. of the Chem. Soc. Chemical Communication (London) pp. 142–143 (1974).
Pudovik et al., Bull. Acad. Sciences of USSR, vol. 27 (2) Part 2, pp. 410–411 (1978).
Wife et al., J. of the Chem. Soc. Chem. Comm., No. 15, pp. 804–805 (1983).
Horspool, J. Chem. Soc., Perkin I, pp. 1113–1117, (1972).
Kosolapoff, J.A.C.S. 72, pp. 4292–4293 (1950).

*Primary Examiner*—Helen M. S. Sneed
*Attorney, Agent, or Firm*—Ronald R. Reper

[57] ABSTRACT

A process is disclosed for the preparation of 1,2-bisphosphine oxides by reacting at least one of certain phosphine oxides with certain oxirane compounds in an aprotic solvent and in the presence of a basic compound.

11 Claims, No Drawings

PROCESS FOR THE PREPARATION OF BISPHOSPHINE DIOXIDES

BACKGROUND OF THE INVENTION

The invention relates to a process for the preparation of a bisphosphine dioxide with formula

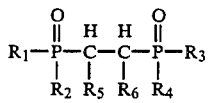

in which $R_1$, $R_2$, $R_3$ and $R_4$, being the same or different, represent substituted or unsubstituted alkyl-, aryl-, alkaryl- or aralkyl groups or an alkylene group is formed by $R_1$ and $R_2$ and/or $R_3$ and $R_4$ respectively, $R_5$ represents H, $R_6$ represents H or a substituted or unsubstituted alkyl-, aryl-, alkaryl- or aralkyl group, or $R_5$ and $R_6$ form an alkylene group, and to bisphosphine dioxides obtained by this process.

Bisphosphines are widely employed as bidentate ligands in transition metal, in particular Group VIII noble metal (e.g. rhodium), catalyzed reactions such as hydrogenation, hydrosilylation and hydrocarbonylation. Owing to the structure of these ligands various electronic or steric influences can be exerted in the close environment of the chelated metal centre. Accordingly, the selectivity of the catalysts strongly depends on the structure of the bisphosphines used as ligands, which structure may e.g. give rise to asymmetric hydrogenation. In this way the hydrogenation of unsaturated comounds to form saturated compounds having optical activity may be achieved. As an example the hydrogenation of substituted acrylic acids and esters to form stereoisomers of amino acids (e.g. phenylalanine, hydroxyphenylalanine, β-indolylalanine and dihydroxyphenylanaline) may be mentioned.

Bisphosphines can be easily prepared from bisphosphine dioxides by well known techniques such as reduction with a mixture of chlorosilanes and trialkylamines, or with aluminum hydride.

Methods for the preparation of bisphosphine dioxides are known, but they are complicated and do not give satisfying yields.

The invention provides an attractive method for the preparation of bisphosphine dioxides in high yields, by reaction of oxiranes with secondary phosphine oxides.

SUMMARY OF THE INVENTION

Accordingly, the invention provides a process for the preparation of a bisphosphine dioxide with formula

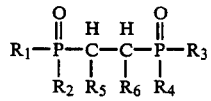

in which $R_1$, $R_2$, $R_3$ and $R_4$, being the same or different, represent substituted or unsubstituted alkyl-, aryl-, alkaryl- or aralkyl groups containing up to about 10, preferably up to about 8 carbon atoms or an alkylene group containing up to about 8 carbon atoms is formed by $R_1$ and $R_2$ and/or $R_3$ and $R_4$ respectively, $R_5$ represents H, $R_6$ represents H or a substituted or unsubstituted alkyl-, aryl-, alkaryl- or aralkyl group, containing up to about 8 carbon atoms or $R_5$ and $R_6$ together form an alkylene group, containing up to about 8 preferably up to about 6 carbon atoms.

by contacting in an aprotic solvent and in the presence of a basic compound an oxirane with formula:

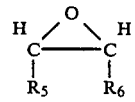

with one or more phosphine oxides with formula:

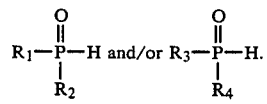

DESCRIPTION OF PREFERRED EMBODIMENTS

In the phosphine oxides with structure

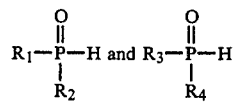

to be used as starting compounds one or more of $R_1$, $R_2$, $R_3$ and $R_4$ very suitably represent a tertiary alkyl group (e.g. tertiary butyl).

Preferably one or more, and in particular all, of $R_1$, $R_2$, $R_3$ and $R_4$ represent a substituted or unsubstituted aryl group, in particular a phenyl group. Substituents of the aryl group may comprise any group which does not interfere with the reaction, such as alkyl groups (e.g. methyl groups), or alkoxy groups, in particular methoxy groups. The substituents may be ortho, para or meta to the site of attachment of the phosphorus atom to the arylgroup. As substituted aryl group the o.methoxyphenyl group is preferred. In the oxirane with structure

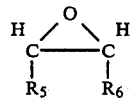

to be used as starting compound $R_6$ preferably represents an alkylgroup such as an ethyl-, propyl- or butyl group, and in particular a methyl group.

As examples of oxiranes in which $R_5$ and $R_6$ form an alkylene group, cyclopentane epoxide and cyclohexane epoxide can be mentioned.

The basic compound to be used very suitably should at least be partially soluble in the aprotic solvent. Alkalimetal alkyls, such as lithium-alkyls e.g. lithium-butyl, are very suitable. Preference is given to metal hydrides in particular to those of the alkali metals such as sodium hydride and lithium hydride.

The basic compound preferably is used in an amount chemically equivalent to the amount of phosphine oxide to be reacted. So in the case where sodium hydride or lithium-butyl is used as basic compound, one mole thereof is preferably used for each mole of phosphine oxide to be reacted.

The reaction rate is dependent on the temperature and the type of aprotic solvent used. Temperatures between ambient and the boiling point of the reaction mixture are very suitable. The reaction runs more smoothly in more polar aprotic solvents than in less polar ones. As more polar aprotic solvents may in particular be mentioned those containing a substituted amide group such as 1.3-dimethyl-2-imidazolidinone and dimethylformamide, the latter being preferred.

It has been found that in less polar solvents, such as hydrocarbons (e.g. hexane) and ethers (e.g. tetrahydrofuran, diethylether) only one molecule of the phosphine oxide reacts with the oxirane, leading to an intermediate compound with formula

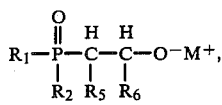

the counter ion M being the metal of the basic compound used (e.g. Li or Na). Even in the case where an excess of one of the organic components is present over the amount needed for the formation of said intermediate compound the reaction does not go further under the conditions used in general viz. atmospheric pressure and a temperature of at most that of the boiling reaction mixture. By replacing the less polar solvent partly or totally by a more polar solvent more phosphine oxide will react with the intermediate compound mentioned above with formation of a bisphosphine dioxide according to the invention, provided sufficient basic compound is available.

The phenomenon described opens up the possibility to prepare bisphosphine dioxides with formula

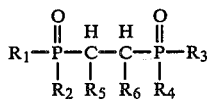

in which $R_3$ is different from $R_1$ as well as from $R_2$. As a matter of course $R_4$ may also be different from $R_1$ as well as from $R_2$, and $R_3$ may also be different from $R_4$.

These compounds may be prepared by reacting one mole of a phosphine oxide with formula

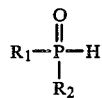

with one mole of an oxirane with formula

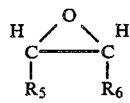

in the presence of at least one equivalent of a basic compound (e.g. sodium hydride or lithium-butyl), in a less polar solvent (as explained above), followed by addition of one mole of a phosphine oxide with formula

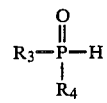

in which $R_3$ is different from as well $R_1$ and $R_2$, and replacement of the less polar solvent by a more polar one (e.g. dimethylformamide). If necessary a further amount of a basic compound which does not react with the more polar solvent is to be added.

It is also possible to isolate the reaction product of one phosphine oxide molecule with one oxirane molecule by acidification of the mixture which contains the intermediate compound and separating off the precipitated compound with formula

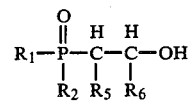

This compound can be converted to a bisphosphine dioxide according to the invention by contacting it in a more polar solvent (e.g. dimethylformamide) with a phosphine oxide and an amount of basic compound which does not react with the more polar solvent at least equivalent to the amounts of this intermediate compound and the phosphine oxide to be reacted together. Alternatively, the said compound with formula

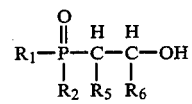

in a less polar solvent may be contacted with a phosphine oxide and a basic compound, followed by addition of a more polar solvent which does not react with the basic compound.

EXAMPLE 1

Preparation of 1-methyl-1,2-bis-(diphenylphosphinyl)ethane 120 mg (5 mmol) of sodium hydride was added to a stirred solution of 1.0 g (5 mmol) diphenylphosphine oxide (in dry dimethylformamide (25 ml)) at room temperature under argon. With evolution of hydrogen a pale yellow solution was formed. The mixture was heated to 60° C. and 145 mg (2.5 mmol) propane epoxide was added. Precipitation of a white solid started immediately, and the reaction was brought to completion by stirring at 60° C. for 2 hours. The reaction mixture was acidified with dilute HCl and extracted with methylene chloride. The organic layer was washed with a 10% solution of sodium carbonate, dried, and the organic solvent was evaporated. Recrystallization of the residue from chloroform-diethylether yielded 0.93 g (84% yield) of the bisphosphine oxide.

EXAMPLE 2

Preparation of 1,2-bis(diphenylphosphinyl)cyclohexane

Sodium hydride (0.34 g; 14.16 mmol) was added to a stirred solution of diphenylphosphine oxide (2.8 g; 13.86 mmol) in dimethylformamide (30 ml) at room temperature under argon. To the yellow solution was then added cyclohexane epoxide (0.68 g; 6.94 mmol) and the reaction mixture was warmed to 70° C. The yellow color slowly faded and after 2 hours a white precipitate had formed. The mixture was cooled, acidified with dilute HCl and the product extracted with chloroform. The removal of all solvents afforded, after recrystallization from chloroformdiethylether, trans-1,2-bis(diphenylphosphinyl)cyclohexane (3.10 g; 93% yield).

EXAMPLE 3

Preparation of 2-diphenyl-phosphinylethanol 6.25 ml of butyl lithium (1.6 molar in hexane) was added to a stirred solution of 2.02 g (10 mmol) diphenylphosphine oxide in dry tetrahydrofuran (100 ml) at room temperature under argon. With the evolution of butane a pale yellow solution was formed. To the yellow solution was added ethylene oxide (2 ml; 50 mmol) and the reaction was stirred for up to two days at room temperature. The reaction mixture was acidified with dilute HCl and extracted with methylene chloride. The organic layer was dried and evaporated. The residue was pure 2-diphenyl-phosphinylethanol which was used as obtained in the following reaction.

Preparation of 1-diphenylphosphinyl, 2-di(o-methoxy)phenylphosphinyl ethane.

6.25 ml of butyl lithium (1.6 molar in hexane) was added to a stirred solution of 1.23 g (5 mmol) 2-diphenylphosphinyl ethanol and 1.31 g (5 mmol) bis o-methoxyphenylphosphine oxide in dry tetrahydrofuran (10 ml) at room temperature under argon. With evolution of butane a pale yellow solution was formed. To the yellow solution was added dry dimethylformamide (100 ml) and the mixture was warmed to 90° C.–100° C. overnight. The reaction mixture was cooled, acidified with dilute HCl and extracted with methylene chloride. The organic layer was washed with a 10% solution of sodium carbonat dried, and the organic solvent was evaporated. Recrystallization of the residue from methylenechloride-diethyl ether yielded 1.6 g (65% yield) of 1-diphenylphosphinyl, 2-di(o-methoxy)phenylphosphinyl ethane.

We claim:

1. A process for the preparation of a bisphosphine dioxide of the formula:

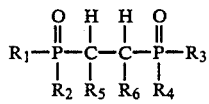

in which $R_1$, $R_2$ and $R_4$ being the same or different and $R_3$ being different than $R_1$ and $R_2$, represent alkyl- arylalkaryl-, alkoxyaryl- or aralkyl groups containing up to about 10 carbon atoms, or an alkylene group containing up to about 8 carbon atoms is formed by $R_1$ and $R_2$ and/or $R_3$ and $R_4$ respectively, $R_5$ represents H, $R_6$ represents H or an alkyl-, aryl-, alkaryl or aralkyl group containing up to about 8 carbon atoms, or $R_5$ and $R_6$ form an alkylene group containing up to about 6 carbon atoms, by contacting in a first stage one mole of a phosphine oxide with formula

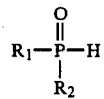

in a solvent having less polarity than the solvent in subsequent second stage with one mole of oxirane with formula

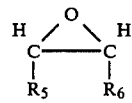

and contacting the reaction product obtained in a second stage in a solvent having more polarity than the solvent in the first stage with one mole of a phosphine oxide with formula

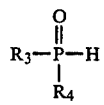

and producing said bisphosphine dioxide.

2. A process according to claim 1, wherein at least one of groups $R_1$, $R_2$, $R_3$ and $R_4$ represent an aryl group, an alkaryl group or an alkoxy-aryl group.

3. A process according to claim 2, wherein at least one of groups $R_1$, $R_2$, $R_3$ and $R_4$ represent an alkoxy-aryl group.

4. A process according to claim 3, wherein at least one of groups $R_1$, $R_2$, $R_3$ and $R_4$ is an o.methoxy-phenyl group.

5. A process according to claim 1, wherein $R_6$ represents an alkyl group.

6. A process according to claim 5, wherein the alkyl group is a methyl group.

7. A process according to claim 1, wherein the basic compound is sodium hydride.

8. A process according to claim 1, wherein the basic compound is butyl lithium.

9. A process according to claim 1, wherein the amount of basic compound used is substantially equivalent to the amount of phosphine oxide to be reacted.

10. A process according to claim 1, wherein the less polar solvent in the first stage consists essentially of a hydrocarbon or an ether or a mixture thereof, and the solvent in the second stage consists essentially of a solvent which contains an amide group.

11. A process according to claim 10, wherein the less polar solvent in the first stage consists of hexane or tetrahydrofuran or a mixture thereof, and the solvent in the second group consists of dimethylformamide.

* * * * *